United States Patent
Crandall

(10) Patent No.: US 6,979,441 B2
(45) Date of Patent: Dec. 27, 2005

(54) METHOD FOR TOPICAL TREATMENT OF CARPAL TUNNEL SYNDROME

(76) Inventor: Wilson T Crandall, P.O. Box 346, Fort Defiane, VA (US) 24482

( * ) Notice: Subject to any disclaimer, the term of this patent is extended or adjusted under 35 U.S.C. 154(b) by 441 days.

(21) Appl. No.: 10/126,034

(22) Filed: Apr. 19, 2002

(65) Prior Publication Data

US 2002/0164389 A1 Nov. 7, 2002

Related U.S. Application Data

(63) Continuation-in-part of application No. 09/395,511, filed on Sep. 14, 1999, now Pat. No. 6,306,383.
(60) Provisional application No. 60/100,530, filed on Sep. 16, 1998, provisional application No. 60/114,813, filed on Jan. 6, 1999, and provisional application No. 60/123,594, filed on Mar. 10, 1999.

(51) Int. Cl.[7] .......................... A61K 31/74; A61K 45/00
(52) U.S. Cl. .................. 424/78.06; 424/78.02; 424/78.03; 424/450; 424/725
(58) Field of Search ..................... 424/78.06, 78.02, 424/78.03, 283.1, 450, 725

(56) References Cited

U.S. PATENT DOCUMENTS 6,284,751 B1 * 9/2001 Aiello et al. ................. 514/183
6,306,383 B1 * 10/2001 Crandall ................... 424/78.06

* cited by examiner

Primary Examiner—Jean C. Witz

(57) ABSTRACT

This invention relates to the topical treatment of the Carpal Tunnel Syndrome by the use of a selected protein kinase C inhibitor and an effective penetrating agent selected from lecithin organogel or poloxamer 407 lecithin organogel. The protein kinase C inhibitors may be selected from sphingosine, sphinganine, phytosphingosine, curcumin, tetrahydrocurcumin, curcuminoids or apigenin.

9 Claims, No Drawings

METHOD FOR TOPICAL TREATMENT OF CARPAL TUNNEL SYNDROME

PRIOR RELATED APPLICATION

The present application is a continuation-in-part of pending U.S. Provisional applications Ser. Nos. 60/100,530, 60/114,813 and 60/123,594 filed on Sep. 16, 1998, Jan. 6, 1999 and Mar. 10, 1999 and U.S. application Ser. No. 09/395,511, filed Sep. 14, 1999 now U.S. Pat. No. 6,306,383, issued Oct. 23, 2001.

TECHNICAL FIELD OF THE INVENTION

The present invention is related to a process and composition for topically inhibiting protein kinase C. More particularly, the present invention relates to topically applying the composition disclosed herein in order to treat the tendons affected by tenosynovitis in Carpal Tunnel syndrome which may cause a compression of the median nerve, and over a protracted period of time a perineural fibrosis which can produce a neuropathy of the median nerve.

BACKGROUND OF THE INVENTION

Mukhtar in Pharmacology of the Skin describes the communication between cells as being mediated by different biomolecules, such as hormones. These so called primary messengers bind to specific receptors on the cell surface. The binding of the primary messenger of a primary messenger to its receptor conveys a certain information to the cell which is subsequently transduced through the membrane by a chain of signaling. This process involves various membrane structures and leads to the activation of an enzyme located at the intracellular side of the membrane. The stimulated enzyme generates a second messenger which evokes the cellular response; in most cases, by the activation of other enzymes. By these steps, the initial extracellular signal is converted into an intracellular signal. This process is called signal transduction.

The inositol cascade represents one of several signal transducing pathways. In its course, 2 second messengers, diacyglycerol (DG) and inositol triphosphate (IP3) are released. DG remains in the membrane and activates protein kinase C (PKC). IP3 acts by releasing calcium ions from their intercellular stores. The calcium ions subsequently evoke the cellular response, mainly by activating PKC.

Protein kinases regulate cellular responses by phosphorylation pathways of substrate proteins (eg. receptors or enzymes) and thereby alter their state of activity. In the case of the inositide cascade, PKC mainly performs this reaction. sphingosine dose-dependently inhibits PKC, but also binds to calmodulin (CaM) function and therefore inhibits CaM function Keratinocyte intercellular adhesion molecule (ICAM-1) is thought to be involved in dermal lymphocyte infiltration. The PKC activating phorbol ester, PMA has been reported to induce the expression of ICAM-1 in normal human keratinocytes. This effect can be blocked by a PKC inhibitor and suggests that PKC might play a role in ICAM-1 expression.

Tendons often pass through a protective sheath where they curve around bones or change directions. Excessive movement of the tendon can cause irritation, and if the friction continues, an over production of synovial fluid can cause tenosynovitis and a compression of the median nerve. Chronic distention of the tendon sheath can produce fibrosis in the carpal canal reducing the space for the flexor tendons, which will irritate the median nerve and produce a perineural fibrosis.

The repetitive hand motion initiates the pathology described above. Musicians, secretaries, athletes, short order cooks, computer programmers, sign language communicators, beauticians, and many workers in industry repeating the same act for extended periods of time.

Protein kinases regulate cellular responses by phosphorylation of substrate proteins (eg, receptors or enzymes) and thereby altering their state of activity. In the case of the inositide cascade, PKC mainly performs this reaction. sphingosine dose-dependently inhibits PKC, but also binds to calmodulin (CaM) function and therefore inhibits CaM function. The PKC activating phorbol ester, PMA has been reported to induce the expression of ICAM-1 in normal keratinocytes. This effect can be blocked by a PKC inhibitor and suggests that PKC might play a regulatory role in ICAM-1 expression.

Phytosphingosine inhibits PKC a and PKC b, as well as many other isoforms of PKC. This would mean that TGF beta would be inhibited so as to stop the excessive collagen production. In addition collagenase would be up regulated which would remodel the pathologically formed collagen. VEGF would be inhibited and this would prevent the synovial sheath from distending from fluid and which leads to tenosynovitis and a compression neuritis, as well as neovascularization of the sheath. TGF beta & PDGF would not be creating a thicker synovial sheath or forming adhesions between the tendon and the synovial sheath. In addition ICAM-1 would be inhibited as would LFA-1 greatly reducing the white blood cells migrating out of the synovial blood vessels. These white cells are greatly responsible for the inflammation and the proliferative changes in the synovial membrane as well as adhesions formed by scar.

TNF a is now recognized as being active in tenosynovitis and responsible for pain. This cytokine would be inhibited also.

At this point medical treatment consist of splints which are first used at night and then during the day if response is not evident. Steroid injections are used several times, rest from repetitive motions on the job and finally surgery when pain and weakness of the hand doesn't respond. Surgery does afford a quick fix, but additional fibrosis occurs and the patient will experience the previous symptoms.

What is needed is a topical Rx which when applied to the wrist will be delivered in an effective concentration so that it will inhibit the cytokines producing the inflammation which is responsible for the tenosynovitis and its compression of the median nerve. In addition TGF beta will be inhibited so that scar will not form. Inhibition of this growth factor up regulates collagenase and scar is remodeled so that the canal returns to its normal width and adhesions of the tendon, synovial membrane and median nerve are eliminated.

It must be emphasized that this syndrome begins with an inflammation of the synovial sheath of the tendon. If the invention were to be used in a preventative manner for workers at higher risk, it would prevent the development of the tenosynovitis. This initiates the syndrome and ultimately leads to the fibrosis in the carpal canal and possible neuropathy of the median nerve with permanent weakness.

A more focused attention in the work place must be made regarding tendon injury which results from repetitive strain injuries These injuries are caused and aggravated by repetitive movements sustained for long periods without adequate rest breaks. This behavior is known to cause tenosynovitis which may lead to Carpal tunnel syndrome. Prevention would be the most enlightened method, but the invention can be used prophylatically also when repetitive strain is not possible to eliminate. Certainly once clinically symptoms are evident, the Rx would be used twice daily for several weeks after symptoms ceased. Carpal tunnel syndrome is the most common hand disorder in Workman's Compensation claims. and its frequency could be dramatically reduced.

What is important to emphasize is that the fibrosis within the canal is stimulated by the tenosynovitis of distended the flexor tendons in the Carpal canal. If this inflammation is inhibited, the disease can not proceed to the formation of scar and the serious consequences of compression neuropathy.

SUMMARY OF THE INVENTION

The present invention provides compositions and an easy to use therapeutic method for inhibiting PKC activity in underlying structures of the skin, as well as the diseases related to it. These processes include inflammatory disease of the tendon and its sheath, tenosynovitis which produces scar and limits the physiological range of motion as well as creating pain The present invention includes a composition for topical inhibition of the effects of PKC activity as a second messenger wherein the molecule or molecules are selected from the group consisting of phytosphingosine, curcuminolds, and tetrahydrocurcumin. Other PKC Inhibitors referenced in U.S. Pat. No. 6,306,383 and provisional patent 09/395,511 filed Mar. 10, 2000 are suitable for this invention and may be used in the invention combined with delivery vehicles and penetrating agents optionally containing lecithin, unhydrogenated or hydrogenated, lecithin organogel, or Pluronic 127 lecithin organogel.

Therapeutically effective amounts of phytosphingosine may be combined at concentrations of 0.1 g to 7.5 g per 100 grams of formulation for topical composition of this invention. Optionally 0.01 g to 7.5 g of tetrahydrocurcumin may be used.

DETAILED DESCRIPTION OF THE INVENTION

Optionally 0.01 g to 7.5 g of tetrahydrocurcumin, or another curcuminoid maybe used by itself or in combination with the phtyosphingosine or another PKC inhibitor known to those skilled in the art. Phtyosphingosine has as broad an activity against the various isoforms of PKC as does sphingosine. Tetrahydrocurcumin also has a broad spectrum of PKC inhibition as well as inhibiting the lipoxyoxygenase pathway and TNF alpha This cytokine has been incriminated in tenosynovitis and is responsible for the in the tendon sheath which limits mobility of the hand. It may also be used in the invention The present invention provides a composition comprising a pharmaceutically effective penetrating agent, and a method for transdermally administering protein kinase C inhibitors. The composition and method of the present invention may be used to treat disease of the tendon and sheath caused by protein kinase C as well as scar produced by distended flexor tendons in the carpal tunnel by transdermal delivery of the desired protein kinase C inhibitor.

The term "condition" means any biological state of a patient. Conditions may be painful and inflammatory.

The ceramides which are present in the compositions of the invention are understood to have a structure which is comparable to that of the ceramides identified as ceramide 1, 2, 3, 4, and 61 and 611. More specifically, the ceramides which are present in the compositions of the invention are understood to comprise ceramides in which the sphingoid base backbone is selected from the group consisting of sphingosine, phytosphingosine, and sphinganine, wherein said sphingoid base backbone is acylated with an acyl or an acyloxyacyl group, wherein said acyl or acyloxylacyl group can have a variable chain length, optionally can have (additional) double bonds, optionally contain a hydroxyl group and optionally can be branched.

Phytosphingosine is the preferred ceramide for this invention. However, other ceramides selected from the group N-tetracosanoyl phytosphingosine, N-stearoyl phytosphingosine, N-oleoyl phytsosphingosine, N-linoleoyl-phytosphingosine, N-(2-hydroxytetracosanoyl), phytosphingosine, N-(2-hydroxyoctdecanoyl) phytosphingosine, N-phytosphingosine, 22(2hydroxyoctdecanoyl) hydroxyoctdecanoyl) phytosphingosine, N-(27-stearoyloxy-hepatoaconsanoyl) phtosphingosine, N__(27-oleoyloxheptacosanoyl) phytosphingosine, N (27-linoleoyoxyheptaconsanoyl) phytosphingosine, N-(23-stearoyloxytricosanoyl) phytosphingosine maybe used.

Sphingoid bases (phytosphingosine, sphingosine and sphinganine ) are present in the stratum corneum in their free form and as constituents of ceramides. In this invention, these lipids. Their analogues, derivatives and reaction products, however, prepared; whether, prepared by chemical, or biochemical reaction, or by microbial fermentation, or isolated from natural sources: have effective performance in use. In particular, ionic salts of the fore mentioned lipids are contemplated in use.

The dried, ground rhizomes of Curcuma longa is a rich source of phenolic compounds or curcuminoids. "Curcuminoids" refers to a group of phenolics present in tumeric, which are chemically related to its principal ingredient, curcumin. Three main compounds were isolated from tumeric: curcumin, demethoxycurcumin, and bis-demethoxycurcumin. All 3 impart a yellow color.

Other curcuminoids may be used also. An example is tetrahydrocurcumin which is a hydrogenated product of curcumin produced by reducing curcumin in an organic solvent using a metal catalyst. It doesn't have a yellow color.

Lecithin is described as a hygroscopic waxy solid which only forms an emulsion after dissolution with an organic solvent. The phosphatidylcholine (PC)may be characterized as amphiphillic because of polar head group is hydrophilic and has lipophilic carbon tails. This amphillic property permits the surface polar heads in the aqueous phase to contract, assuming the shape of a sphere. Lecithin emulsions are aggregates of micelles in water and inherently have a poor stability. Williman et al, Journal of Pharmaceutical Sciences 81:871–874 (1993) found that PC, with a minimum of 95%, formed giant-like spaghetti-like micellar gels after it was dissolved in an appropriate nontoxic organic solvent. This structure is called a lecithin organogel and is thought to have a linear rather than the usual spherical structure. Soy lecithin containing less than 95% PC will not gel. PC of 95% purity is expensive.

A preferred phospholipid for use in the present invention is phosphatidylcholine, also known as lecithin. Stedman's medical dictionary (21 st ed, pg. 879) define lecithin as any group of phospholipids which upon hydrolysis yield 2 fatty acids molecules and a molecule each of glycerophosphoric acid and choline. There are several varieties of lecithin, soybean is the preferred lecithin and is the most economical. Lecithins are also found in nervous tissue, hepatic tissue, cardiac tissue, and egg yolks. It is therefore understood that any reference to lecithin or phosphatidylcholine is intended to include any combination of lecithin-like phospholipid compounds as well known in the art. Examples of other phospholipids which can be used in accordance with the present invention include phosphatidylinositol, phosphatidylethanoloamine, phoshatidylserine, and phosphatidic acid. A mixture of any of the above phospholipids may also be employed and are present in natural soy lecithins.

A preferred penetrating agent and delivery vehicle is lecithin organogel which is a combination of equal parts of phosphatidylcholine and an organic solvent eg. isopropyl palmitate, isopropyl myristate or ethanol and a small amount of water to make the gel. Lecithin organogels have been described as vehicles that are useful in facilitating the delivery of low molecular weight compounds transdermally (Williman et al, Journal of Pharmaceutical Sciences 81:871–874 (1992) which is incorporated herein by reference). The lecithin organogels are obtained by adding small amounts of water to a solution of phosphatidylcholine with equal parts of an organic solvent .

Preparation of a variety of lecithin gels all of which are appropriate in practicing the invention, are described in Scartazzini, et al Journal of Physical Chemistry 92:829–833, 1988, and Luisi. P. L., Colloid and Polymer Science 268; 356–374 1990, both of which are incorporated herein by reference in their entirety. The lecithin organogel preferably comprises 1:1 to 1.5:5 (weight/volume) of Phospholipon 90 (American lecithin, Oxford, Conn.) isopropyl myristate or isopropyl palmitate. Other penetrating agents may be used in the composition of the present invention.

A gelling agent optionally may be added to the formulation. Gelling agents that are suitable include, but are not limited to poloxamer 407 lecithin organogel, cellulose ethers, aliginates, polyacrylates (Carbapol polymers), bentonite, gelatin, magnesium aluminumsilicate, tragacanth, pyrrolidone, polyvinylalcohol, polyoxyetherethylene/polyoyxpropylene and aluminum silicate.

The term "PLURONIC" refers to a poloxamer compound sold collectively under the trademark PLURONIC (BASF, Parsippany, N.J.) PLURONIC 127 (PL 127) corresponds to poloxamer 407, a polyoxypropylene-polyoxethylene block copolymer. Schmolka describes this block polymer in the Journal of Biomedical Materials Research 6:571–582.1972. Other PLURONICS may be used in the present invention. As used in this application, the terms PLURONICS organogel, poixamer organogel, and polyoxyethylene-polyoxypropylene organogel are synonymous.

Another penetrating agent of the present invention includes lecithin dissolved in equal parts of an organic solvent such as isopropyl myristate, isopropyl palmitate or another solvent may be used by those familiar with the art.

The preferred concentration of poloxamer 407 is 15 to 25%, with the most preferred concentration of poloxamer 407 about 17.5% to 18%. Usually a 20% to 40% solution of PLURONIC is used to create the gel. The higher the concentration of PLURONIC solution, the higher the % of actives may be used. A 40% PLURONIC solution requires 44 ml to achieve a 17.5% PLURONIC. Thus 56% of the 100 g formulation could be actives.

To make a 40% PL 127 solution 40 g of PLURONIC would be added to 60 g of distilled water. This is then placed in the refrigerator and stirred until it is dissolved. The advantage of a 40% PL 127 concentration is that only 45 ml of the solution would be required to produce a formulation with a concentration of 17.5% PLURONIC.

The preferred concentration of lecithin is 5% to 18%. The active is made soluble in the lecithin and an amount of poloxamer 407 is added to the lecithin and active(s) to produce a final concentration of poloxamer 407 of 17.5% to 20%. Purified water and any other agent known in the art maybe added to the formulation to produce a 100 grams. This mixture is called a PLURONIC organogel (PLO) finally surgery when pain and weakness of the hand occur.

What is needed is a topical Rx which when applied to the wrist will be delivered in an effective concentration so that it will inhibit the inflammation producing the tenosynovitis and its compression of the median nerve and dissolution of the scar formed. If the invention were to be used daily it will prevent the development of the tenosynovitis. Furthermore it will inhibit collagen formation and up regulate collagenase so that scar formed will be remodeled. After surgical treatment of the disease, fibrosis frequently forms and this collagen undergoes remodeling also. This way the compression neuritis created by tenosynovitis of the tendons or the scar resulting from surgery may be prevented.

The term "pharmacologically active agent" relates to any chemical material or compound suitable for topical administration which includes any desired local effect on animal or human tissues contacted therewith.

The term "Topical" application is used to mean a local administration of the composition and its various embodiments. For example, in the treatment of carpal tunnel.

The term "pharmaceutical effective carrier" is used to mean any liquid, gel, salve, solvent, diluent, fluid, ointment base, liposome, micelle, giant reverse micelle, poloxamer lecithin organogel The term "pharmaceutically effective carrier" is used herein to mean any liquid, gel, salve, solvent, diluent, fluid, ointment base. liposome, micelle, giant reverse micelle, and the like. Liposomes are described in detail by Oleniacz in U.S. Pat. No. 3,957,971, the entirety of which is hereby incorporated by reference. The carrier must also be suitable for use in contact with living animals or human tissue without causing adverse physiological responses , and which does not interact with other components of the composition in a deleterious manner.

By the term "therapeutically effective amount" of a molecule, drug, or pharmacologically active agent is meant a nontoxic, but sufficient amount to provide the desired therapeutic effect.

The "enhanced penetration" caused by compositions of this invention as used in topical application with this method, means increased penetration into the skin, and is achieved with compounds such as lecithin organogel, poloxomer 407 lecithin organogel, including but not limited to phosphatidylcholine, phoshatidylethanolamine, phoshatidylserine, phosphatidylinositol, and phosphatidic acid optionally combined with PLURONIC 127, ethoxydiglycol, ethanol, or cholesterol. Enhanced penetration can be observed in many ways known to those skilled in the art.

1 nM dissodium edetate is added to the gel so as to minimize auto oxidation. Other anti-oxidants may be used are vitamin E, vitamin C (ascorbyl palmitate), grape see extract 250 mg of tetrahydrocurcumin is a powerful antioxidant as well as powerful antioxidants and potent chelating agent.

Therapeutically effective amounts of phytosphingosine may be formulated at concentrations of 0.01 to 7.5 g per 100 grams of formulation. 1.5 g. to 2.5 g phytosphingosine is placed in a beaker with 8.5 g to 10 g of lecithin. Phosphal 75 (American lecithin Co, Oxford, Conn.) or Phospholipon 90 which can be dissolved by ethanol after it is diced into very small fragments. The Phospsphal 75 contains 75% phosphatidylcholine and the Phospholipon contains 90%. The mixture is heated to 80 C. After the components dissolve, a small amount of distilled water is added to the mixture as it is mechanically stirred. The ceramide is driven between the fatty acids tails of the phosphatidylcholine by hydrophobic forces. This is continued until the mixture turns a milky coloration. At this point power stirring may be used.

A solution of PLURONIC 127 is added to the mixture to provide a concentration of the PL 127 about 17.5% to 18%. Ceramides are very insoluble and concentration up to 4% has been achieved in the above manner.

3.5 g to 7.5 g tetrahydrocurcumin is placed in a beaker with 10 ml of ethanol and heated to 70 C. with mechanical stirring. Upon dissolution 8.5 g to 10 g of Phosphal 75% (American lecithin Co. Oxford, Conn.) Phospholipon may also be used at 8.5 g to 10 g. The Phospholipon must be reduced to small pieces to facilitate dissolution. Once the lecithin is dissolved mechanical stirring is used to equally distribute the active. Upon cooling 44 ml of PLURONIC 40% are added and mechanically stirred to insure proper distribution. Distilled water may be added qs 100 g. Preservation is accomplished as described as follows.

Preservation must be aggressively done in that the formulation has a high concentration of lipids. Propylparaben is added at 0.1 g per 100 g of formulation. methoxyparaben is added at 0.25 to 0.45% Finally DMDM Hydantoin is added at 0.25 ml per 100 g of formulation. 1 mM EDTA may be used as a chelating agent. 500 mg of vitamin E is added as an antioxidant. 250 mg tetrahydrocurcumin maybe added as an antioxidant and chelating agent. A bottle with a fine tip dispenser is preferable so that the formulation isn't constantly being contaminated by the patient.

EXAMPLE 1

A women who had previously sought professional help for a tingling, pain and weakness in her hand was diagnosed as having carpal tunnel. She was treated conservatively and it recurred. This lady worked in a Commission for Workman's compensation and had a great of experience with carpal tunnel. She was given a gel of 1.5% phytosphingosine in poloxamer 407 lecithin organogel. The gel was applied at the wrist and symptoms improved within 2 weeks. She continued treatment for another 2 weeks and has not had a recurrence since March '99.

EXAMPLE 2

The niece of this lady worked in an office where the computer was a major part of her day. She described the earlier symptoms of carpal, tingling and mild pain. Due to a lack of insurance she elected to use her aunts Rx. I did caution her that this had to be used several weeks past cessation of symptoms and that a physician should be consulted. Her profession is at high risk for carpal tunnel syndrome.

EXAMPLE 3

The daughter of a physician had 3 previous carpal tunnel surgeries and the problem returned. She was evaluated by the orthopedic surgeon who had performed the previous surgery and he recommended that surgery be done again. Her father suggested that she try the phytosphingosine in an effort to avoid surgery. 1.4% phytosphingosine was prepared in a poloxamer 407 lecithin organogel. Her progress was very gratifying in that she was able to play tennis 4 weeks after beginning the Rx. She was instructed to use the RX for 1 month after the cessation of symptoms.

EXAMPLE 4

A horticulutist complained of a swelling on the dorsum of the lower arm and pain in the hand so that she couldn't abduct the thumb. A swelling along the tendon sheath of the extensor pollicis longus was variable $2^{nd}$ to the amount of use. Finally an Orthopedic surgeon was consulted and he diagnosed stenosing tenosynovitis. She was to use a splint for 1 month, but the pain and weakness remained remained. The orthopedic surgeon told her that it would take 1 year for the weakness and pain to not be evident.

She was given 7.5% tetrahydrocurcumin in a poloxamer lecithin organogel and was told to use it bid. Within 2 weeks she could abduct the thumb and the synovial effusion was evident only after she exercised which she had been instructed not to. She estimated that in one month normal function of the arm and hand returned.

Whereas this case is not Carpal tunnel syndrome, the pathogenesis of the tenosynovitis is identical. Stenosing tenovaginitis is also seen in carpal tunnel syndrome. This women also suffered weakness and pain in the forearm as well as in the hand due to the tenosynovitis. She could originally could not abduct the thumb from the first digit the pain was so excruciating.

PKC inhibition of the VEGF and TGF beta were fundamental for her recovery. In addition extravasation of white blood cells which produce free radicals and inflammatory cytokines are prevented by the inhibition of ICAM-1 and LFA-1.(adhesion molecules).

What is important is that the attending physician told this women that it would be 1 year for recovery and that she couldn't use the arm in her work. The reason being excessive use of the muscle and tendon would produce a friction rub which initiates an inflammation of the synovial lining and progresses to a tenosynovitis and a repetition of the clinical symptoms. This is a identical in the etiology of carpal tunnel syndrome.

What is claimed is:

1. A method for treating carpal tunnel syndrome comprising the steps of topically applying to the afflicted area an effective amount of a Protein Kinase C (PKC) inhibitor selected from the group consisting of phytosphingosine, sphingosine, sphinganine, tetrahydrocurcumin, and a curcumin analogue and a pharmaceutically acceptable penetrating agent selected from the group consisting of lecithin organogel and Poloxamer 407 lecithin organogel.

2. The method of claim 1, wherein the flexor tendons of the hand are treated by applying the PKC inhibitor in a pharmaceutically acceptable penetrating agent on the medial wrist at the entrance to the carpal canal.

3. The method of claim 1 wherein the carpal tunnel and the tendon sheath are treated by applying the PKC inhibitor in a pharmaceutically acceptable penetrating agent on the medial wrist at the entrance to the carpal tunnel.

4. The method according to claim 1, wherein said pharmaceutically acceptable penetrating agent is in the form of selected from the group consisting of a gel, a cream, a spray, a salve, a balm, a liposome, and a micelle.

5. The method according to claim 1, wherein the Protein Kinase C inhibitor is phytosphingosine.

6. The method according to claim 1, wherein the Protein Kinase C inhibitor is sphingosine.

7. The method according to claim 1, wherein the Protein Kinase C inhibitor is sphinganine.

8. The method according to claim 1, wherein the Protein Kinase C inhibitor is tetrahydrocurcumin.

9. The method according to claim 1, wherein the Protein Kinase C inhibitor is a curcumin analogue.

* * * * *